US012594085B2

(12) United States Patent
Franco

(10) Patent No.: US 12,594,085 B2
(45) Date of Patent: Apr. 7, 2026

(54) SHOCK WAVE CATHETER WITH SHOCK ABSORBER

(71) Applicant: Shockwave Medical, Inc., Santa Clara, CA (US)

(72) Inventor: Jason B. Franco, Milpitas, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 0 days.

(21) Appl. No.: 18/524,660

(22) Filed: Nov. 30, 2023

(65) Prior Publication Data

US 2025/0176986 A1      Jun. 5, 2025

(51) Int. Cl.
*A61B 17/22*          (2006.01)
*A61B 17/00*          (2006.01)

(52) U.S. Cl.
CPC .................. *A61B 17/22022* (2013.01); *A61B 2017/00929* (2013.01); *A61B 2017/22062* (2013.01)

(58) Field of Classification Search
CPC ........ A61B 17/22022; A61B 17/22012; A61B 17/2202; A61B 2017/00929; A61B 2017/22062; A61B 2017/22025; A61B 2017/22021; A61B 2017/22051
See application file for complete search history.

(56) References Cited

U.S. PATENT DOCUMENTS

| 2,916,647 A | 12/1959 | George |
| 3,412,288 A | 11/1968 | Ostrander |
| 3,413,976 A | 12/1968 | Roze |
| 3,524,101 A | 8/1970 | Barbini |
| 3,583,766 A | 6/1971 | Padberg |
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |

(Continued)

FOREIGN PATENT DOCUMENTS

| AU | 2009313507 B2 | 11/2014 |
| AU | 2013284490 B2 | 5/2018 |

(Continued)

OTHER PUBLICATIONS

International Search Report and Written Opinion received for PCT Patent Application No. PCT/US2023/082082 mailed on Aug. 27, 2024, 8 pages.

*Primary Examiner* — Brigid K Byrd
(74) *Attorney, Agent, or Firm* — Morrison & Foerster LLP

(57) ABSTRACT

A shock wave catheter includes an elongate member and a shock wave emitter assembly located at a distal region of the elongate member. The shock wave emitter assembly includes a shock absorber made of a low durometer material. A shock wave catheter system includes a shock wave catheter with a shock absorber and a high voltage power supply configured to generate high voltage pulses. A method for treating a lesion in a body lumen includes generating shock waves with a shock wave catheter system that includes a shock wave catheter with a shock absorber.

15 Claims, 8 Drawing Sheets

(56)                    References Cited

U.S. PATENT DOCUMENTS

| | | | |
|---|---|---|---|
| 4,741,405 A | 5/1988 | Moeny et al. |
| 4,809,682 A | 3/1989 | Forssmann et al. |
| 4,813,934 A | 3/1989 | Engelson et al. |
| 4,878,495 A | 11/1989 | Grayzei |
| 4,890,603 A | 1/1990 | Filler |
| 4,900,303 A | 2/1990 | Lemelson |
| 4,911,147 A | 3/1990 | Washizuka |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A * | 5/1995 | Winkler ............ A61B 18/1492 |
| | | 607/116 |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,077,236 A | 6/2000 | Cunningham |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Hakala et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,554,815 B2 | 1/2017 | Adams |
| 9,642,673 B2 | 5/2017 | Adams et al. |
| 9,993,292 B2 | 6/2018 | Adams et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Hawkins et al. |
| 10,709,462 B2 | 7/2020 | Nguyen et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,478,261 B2 | 10/2022 | Nguyen |
| 11,534,187 B2 | 12/2022 | Bonutti |
| 11,596,423 B2 | 3/2023 | Nguyen et al. |
| 11,596,424 B2 | 3/2023 | Hakala et al. |
| 11,622,780 B2 | 4/2023 | Nguyen et al. |
| 11,696,799 B2 | 7/2023 | Adams et al. |
| 11,771,449 B2 | 10/2023 | Adams et al. |
| 2001/0044596 A1 | 11/2001 | Jaafar |
| 2002/0045890 A1 | 4/2002 | Celliers et al. |
| 2002/0082553 A1 | 6/2002 | Duchamp |

(56)        References Cited

U.S. PATENT DOCUMENTS

| | | |
|---|---|---|
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157991 A1 | 6/2012 | Christian |
| 2012/0203255 A1 | 8/2012 | Hawkins et al. |
| 2012/0253358 A1 | 10/2012 | Golan et al. |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |

| | | | |
|---|---|---|---|
| 2014/0039513 A1* | 2/2014 | Hakala | A61B 17/2202 |
| | | | 606/128 |
| 2014/0046229 A1* | 2/2014 | Hawkins | A61B 17/22022 |
| | | | 601/46 |
| 2014/0214061 A1 | 7/2014 | Adams et al. | |
| 2015/0320432 A1 | 11/2015 | Adams | |
| 2016/0151081 A1 | 6/2016 | Adams et al. | |
| 2016/0324534 A1 | 11/2016 | Hawkins et al. | |
| 2017/0135709 A1 | 5/2017 | Nguyen et al. | |
| 2017/0311965 A1 | 11/2017 | Adams | |
| 2018/0116717 A1* | 5/2018 | Taff | A61B 18/1492 |
| 2021/0085383 A1 | 3/2021 | Vo et al. | |
| 2021/0137543 A1* | 5/2021 | Warlick | A61B 17/22004 |
| 2021/0338258 A1 | 11/2021 | Hawkins et al. | |
| 2022/0015785 A1 | 1/2022 | Hakala et al. | |
| 2022/0240958 A1 | 8/2022 | Nguyen et al. | |
| 2022/0304712 A1* | 9/2022 | Thirumalai | A61N 7/02 |
| 2023/0043475 A1 | 2/2023 | Adams | |
| 2023/0107690 A1 | 4/2023 | Nguyen | |
| 2023/0165598 A1 | 6/2023 | Nguyen et al. | |
| 2023/0293197 A1 | 9/2023 | Nguyen et al. | |
| 2023/0310073 A1 | 10/2023 | Adams et al. | |
| 2023/0329731 A1 | 10/2023 | Hakala et al. | |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| CN | 115175625 A | 10/2022 |
| CN | 116942250 A | 10/2023 |
| DE | 3038445 A1 | 5/1982 |
| DE | 202006014285 U1 | 11/2010 |
| EP | 0442199 A2 | 8/1991 |
| EP | 0571306 A1 | 11/1993 |
| EP | 623360 A1 | 11/1994 |
| EP | 0647435 A1 | 4/1995 |
| EP | 2253884 A1 | 11/2010 |
| EP | 2362798 B1 | 4/2014 |
| JP | S62-099210 U | 6/1987 |
| JP | S62-275446 A | 11/1987 |
| JP | H03-63059 A | 3/1991 |
| JP | H06-125915 A | 5/1994 |
| JP | H07-47135 A | 2/1995 |
| JP | H08-89511 A | 4/1996 |
| JP | H10-99444 A | 4/1998 |
| JP | H10-314177 A | 12/1998 |
| JP | H10-513379 A | 12/1998 |
| JP | 2002538932 A | 11/2002 |
| JP | 2004081374 A | 3/2004 |
| JP | 2004357792 A | 12/2004 |
| JP | 2011520248 A | 12/2004 |
| JP | 2005501597 A | 1/2005 |
| JP | 2005095410 A | 4/2005 |
| JP | 2005515825 A | 6/2005 |
| JP | 2006516465 A | 7/2006 |
| JP | 2007289707 A | 11/2007 |
| JP | 2007532182 A | 11/2007 |
| JP | 2008506447 A | 3/2008 |
| JP | 2011513694 A | 4/2011 |
| JP | 2011524203 A | 9/2011 |
| JP | 2011528963 A | 12/2011 |
| JP | 2012505050 A | 3/2012 |
| JP | 2012508042 A | 4/2012 |
| JP | 2015525657 A | 9/2015 |
| JP | 2015528327 A | 9/2015 |
| JP | 6029828 B2 | 11/2016 |
| JP | 6081510 B2 | 2/2017 |
| WO | WO-1989011307 A1 | 11/1989 |
| WO | WO-1996024297 A1 | 8/1996 |
| WO | WO-1999000060 A1 | 1/1999 |
| WO | WO-1999002096 A1 | 1/1999 |

(56)         References Cited

FOREIGN PATENT DOCUMENTS

| WO | WO-2000056237 A2 | 9/2000 |
|----|------------------|--------|
| WO | WO-2004069072 A2 | 8/2004 |
| WO | WO-2005099594 A1 | 10/2005 |
| WO | WO-2005102199 A1 | 11/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 | 10/2009 |
| WO | WO-2009126544 A1 | 10/2009 |
| WO | WO-2009136268 A1 | 11/2009 |
| WO | WO-2009152352 A2 | 12/2009 |
| WO | WO-2010014515 A2 | 2/2010 |
| WO | WO-2010054048 A2 | 9/2010 |
| WO | WO-2011006017 A1 | 1/2011 |
| WO | WO-2011094111 A2 | 8/2011 |
| WO | WO-2011143468 A2 | 11/2011 |
| WO | WO-2012025833 A2 | 3/2012 |
| WO | WO-2013059735 A1 | 4/2013 |
| WO | WO-2014025397 A1 | 2/2014 |
| WO | WO-2014025620 A1 | 2/2014 |
| WO | WO-2015017499 A1 | 2/2015 |
| WO | WO-2019099218 A1 | 5/2019 |

* cited by examiner

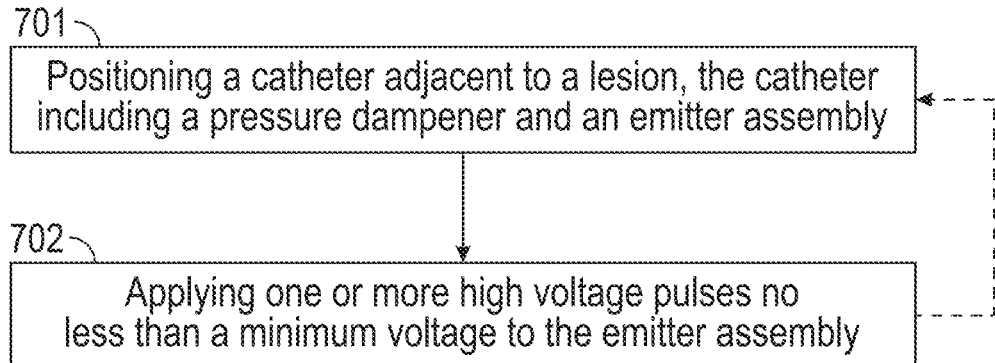

701 ⟍

| Positioning a catheter adjacent to a lesion, the catheter including a pressure dampener and an emitter assembly |

702 ⟍

| Applying one or more high voltage pulses no less than a minimum voltage to the emitter assembly |

FIG. 7

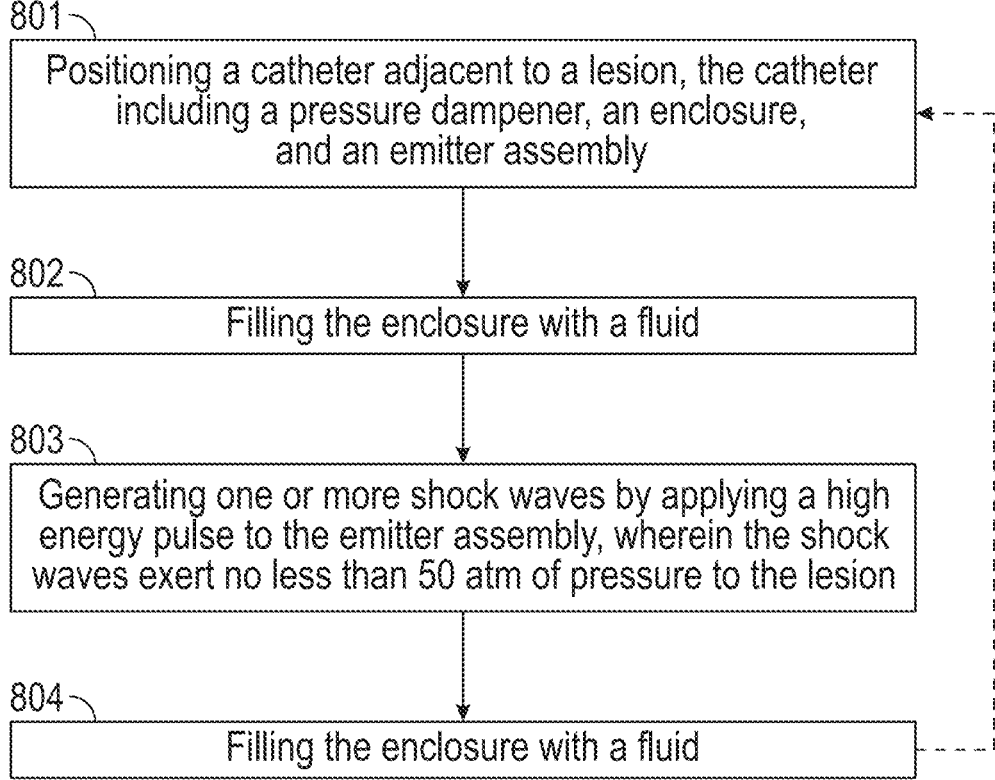

801 ⟍

| Positioning a catheter adjacent to a lesion, the catheter including a pressure dampener, an enclosure, and an emitter assembly |

802 ⟍

| Filling the enclosure with a fluid |

803 ⟍

| Generating one or more shock waves by applying a high energy pulse to the emitter assembly, wherein the shock waves exert no less than 50 atm of pressure to the lesion |

804 ⟍

| Filling the enclosure with a fluid |

FIG. 8

SHOCK WAVE CATHETER WITH SHOCK ABSORBER

FIELD

The present disclosure relates generally to the field of medical devices and methods, and more specifically to acoustic pressure wave generating assemblies for inclusion in catheter devices used for treating lesions in a body lumen, such as calcified lesions and occlusions in vasculature.

BACKGROUND

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than 10 atm), causing the balloon to expand in a vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a fluid that can generate acoustic shock waves that modify the calcified plaque. IVL devices vary in design with respect to the energy source used to generate the acoustic shock waves, with two exemplary energy sources being electrohydraulic generation and laser generation.

For electrohydraulic generation of acoustic shock waves, a conductive solution (e.g., saline) may be contained within an enclosure that surrounds electrodes or can be flushed through a tube that surrounds the electrodes. The calcified plaque modification is achieved by creating acoustic shock waves within the catheter by an electrical discharge across the electrodes. The energy from this electrical discharge enters the surrounding fluid faster than the speed of sound, generating an acoustic shock wave. In addition, the energy creates one or more rapidly expanding and collapsing vapor bubbles that generate secondary shock waves. The shock waves propagate radially outward and modify calcified plaque within the blood vessels. For laser generation of acoustic shock waves, a laser pulse is transmitted into and absorbed by a fluid within the catheter. This absorption process rapidly heats and vaporizes the fluid, thereby generating the rapidly expanding and collapsing vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential energy sources to create IVL shock waves. Other energy sources are possible to create IVL shock waves, including piezoelectric sources.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel tissue or non-calcified plaque. Moreover, IVL does not carry the same degree of risk of perforation, dissection, or other damage to vasculature as atherectomy procedures or angioplasty procedures using cutting or scoring balloons.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, a catheter is advanced over a guidewire through a patient's vasculature until it is positioned proximal to and/or aligned with a calcified lesion in a body lumen. The balloon is then inflated with a fluid so that the balloon expands (e.g., to a relatively low pressure of 2-4 atm) to contact the lesion but is not inflated to a pressure that substantively displaces the lesion. Voltage pulses can then be supplied to the emitters (e.g., by applying a voltage across one or more electrode pairs of an emitter) to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the lumen. Alternative devices to deliver IVL therapy can be within a closed volume other than an angioplasty balloon, such as a cap, balloons of various compliances, or other enclosures.

Efforts have been made to improve the design of electrode assemblies included in shock wave and directed cavitation catheters. For instance, low-profile electrode assemblies have been developed that reduce the crossing profile of a catheter and allow the catheter to more easily navigate calcified vessels to deliver shock waves in more severely occluded regions of vasculature. Examples of low-profile electrode designs can be found in U.S. Pat. Nos. 8,888,788, 9,433,428, and 10,709,462, and in U.S. Publication No. 2021/0085383 all of which are incorporated herein by reference. Other catheter designs have improved the delivery of shock waves, for instance, by specific electrode construction and configuration thereby directing shock waves in a forward direction to break up tighter and harder-to-cross occlusions in vasculature. Examples of forward-firing catheter designs can be found in U.S. Pat. Nos. 10,966,737, 11,478,261, and 11,596,423 and U.S. Publication Nos. 2023/0107690 and 2023/0165598, all of which are incorporated herein by reference.

For treating aortic valve stenosis and other larger body lumens, conventional IVL devices may not be as effective. Previous efforts to implement IVL for treating aortic valves have employed, for example, multiple IVL balloons, as described in U.S. Pat. No. 9,554,815, which is incorporated herein by reference. The sonic output from a radially propagating shock wave emitter decays with distance; thus, for treating aortic valve stenosis or larger vessels (e.g., carotid arteries, iliac arteries) with a conventional IVL device, a relatively higher sonic output may be required for shock wave generating emitters to effectively modify calcified lesions. Alternatively, a relatively higher number of shock wave pulses may be used to treat a calcified lesion in a larger vessel than in a smaller vessel. Physicians face a similar problem when treating eccentric calcified lesions (i.e., lesions where calcium buildup is predominantly along one side of the vessel). When an IVL balloon is inflated in such cases, shock wave emitters may be pushed farther away from the eccentric lesion to be treated.

However, increasing the sonic output from a shock wave emitter may lead to degradation of the emitter and faster failure of the device. One reason for this failure is that increasing the sonic output amplifies the pressures exerted on various structural aspects of the device (e.g., seals, insulating layers, etc.). In particular, past IVL emitters have included polyimide or similar materials with high break-down voltage as an electrically insulating material. Polyimide may be favored for intravascular applications, because it can be made very thin, which is useful for decreasing the overall profile of the IVL catheter and has been shown to be an effective material for use in conventional IVL therapy. Polyimide may also be favored for its high heat resistance (e.g., greater than 250 degrees Celsius). But to meet (a) the durability requirements of IVL catheters with higher sonic output (e.g., to withstand the increased amounts of plasma, pressure, and heat produced during higher pressure shock wave generation) and (b) the longevity requirements of increasing the number of shock wave pulses, improvements to conventional IVL catheters are required.

SUMMARY

According to an aspect of the disclosure, an intravascular lithotripsy (IVL) catheter may include a shock wave generating region that includes a conductive wire, an inner tube, a shock absorber, and an outer band. The inner tube and the outer band may be electrically configured to form an electrode pair where applying a voltage across the electrode pair leads to the generation of a shock wave.

According to an aspect of the disclosure, an IVL catheter may include a shock wave generating region that includes a conductive wire, a shock absorber, and an outer band. A distal end of the conductive wire and the outer band may be electrically configured to form an electrode pair where applying a voltage across the pair leads to the generation of a shock wave.

According to an aspect of the disclosure, an IVL catheter may include a shock wave generating region that includes a conductive wire, an inner tube, an outer band, and an encasing adhesive, where the inner tube and the outer band form an electrode pair. The encasing adhesive may be made of a material chosen to withstand the pressure, plasma, and/or heat generated when a high voltage (e.g., greater than 6 kV) is applied across the electrode pair.

In any of these examples, a catheter for treating lesions in a body lumen may include an elongate member and at least one shock wave emitter assembly mounted over a distal portion of the elongate member. The shock wave emitter assembly may include an electrode pair including an inner electrode and an outer electrode and may be configured to generate a shock wave when a voltage is applied across the electrode pair. The catheter may further include a shock absorber located at least partially between the inner electrode and the outer electrode and surrounding the inner electrode. The shock absorber may have an aperture aligned with the inner electrode and may include a polymer material having a Shore A hardness value no greater than 100. In any of these examples, the polymer material may be a thermoplastic polyurethane. In any of these, the polymer material may have a Shore A hardness value no less than 50. In any of these examples, the polymer material may have a Shore A hardness value no greater than 90. In any of these examples, the catheter may include an enclosure that at least partially surrounds the shock wave emitter assembly, wherein shock waves are transmitted through a wall of the enclosure. In any of these examples, the enclosure may include a balloon (e.g., an angioplasty balloon). In any of these examples, the polymer material may be an electrically insulating material. In any of these examples, the at least one shock wave assembly may be electrically connected to a power supply configured to generate a generator voltage no less than 6 kV.

In any of these examples, a catheter system for treating lesions in a body lumen may include a catheter and a power supply. The catheter may include an elongate member, at least one shock wave emitter assembly mounted over a distal portion of the elongate member, the shock wave emitter assembly including an inner electrode, a shock absorber at least partially surrounding the inner electrode and having a shock absorber aperture aligned with the inner electrode, and a conductive band comprising an outer electrode that is aligned with the shock absorber aperture, the inner electrode and the outer electrode forming an electrode pair. The power supply may be electrically connected to the at least one shock wave emitter assembly and may be configured to supply a voltage no less than 6 kV to the shock wave emitter assembly. In any of these examples, the shock absorber includes a polymer material. In any of these examples, the shock absorber may include a thermoplastic polyurethane. In any of these examples, the polymer material may have a Shore A hardness value no less than 50. In any of these examples, the polymer material may have a Shore A hardness value no greater than 90. In any of these examples, the polymer material may be an electrically insulating polymer material. In any of these examples, the catheter may include an enclosure that at least partially surrounds the shock wave emitter assembly and shock waves are transmitted through a wall of the enclosure. In any of these examples, the enclosure may include a balloon (e.g., an angioplasty balloon). In any of these examples, the power supply may be configured to generate a generator voltage no less than 10 kV. In any of these examples, the shock absorber may have a thickness no less than 0.25 mm and no greater than 1.0 mm.

In any of these examples, a catheter system for treating lesions in a body lumen may include catheter and a power source. The catheter may include a distal region with a shock wave generating region and a shock absorber located at the distal region and contacting the shock wave generating region. The power source may provide energy to the shock wave generating region. The shock absorber may include a thermoplastic polyurethane. In any of these examples, the thermoplastic polyurethane may have a Shore A hardness value no greater than 90. In any of these examples, the thermoplastic polyurethane may have a Shore A hardness value no less than 50. In any of these examples, the catheter may further include an enclosure sealed to the distal region and surrounding and separated from the shock wave generating region.

In any of these examples, a catheter for treating lesions in a body lumen may include an elongate member and at least one shock wave emitter assembly located at a distal portion of the elongate member. The shock wave emitter assembly may include an electrode pair that has a first electrode electrically connected to a high voltage power source and a second electrode spaced apart from the first electrode and electrically connected to the high voltage power source. The shock wave emitter assembly may be configured to generate a shock wave when a voltage is applied across the electrode pair. The shock wave emitter assembly may include a shock absorber at least partially located between the first electrode and the second electrode. The shock absorber may include a polymer material having a Shore A hardness value no greater than 100 and the first electrode may include an edge of a conductive sheath.

In any of these examples, a catheter for treating lesions in a body lumen may include an elongate member and a plurality of axially aligned shock wave emitter assemblies located at a distal portion of the elongate member. Each of the shock wave emitter assemblies may include an electrode pair having a first electrode electrically connected to a high voltage power source and a second electrode spaced apart from the first electrode and electrically connected to the high voltage power source. The shock wave emitter assembly may be configured to generate a shock wave when a voltage is applied across the electrode pair. Each shock wave emitter assembly may further include a shock absorber at least partially located between the first electrode and the second electrode. The shock absorber may include a polymer material having a Shore A hardness value no greater than 100.

In any of these examples, a method of treating a lesion in a body lumen may include: positioning a catheter adjacent to the lesion, the catheter including an emitter assembly with at least one shock wave generating region having a shock absorber made at least in part of a material having a Shore A hardness no greater than 100; and applying a high voltage pulse of no less than 6 kV to the emitter assembly. In any of these examples, the shock absorber may be made of a material having a Shore A hardness no greater than 90. In any of these examples, the high voltage pulse may be no less than 10 kV. The shock absorber material may be a thermoplastic polyurethane. The shock absorber material may be an electrically insulating material. The catheter may further include an enclosure and the method may include the step of inflating the enclosure to a pressure no more than 5 atm.

In any of these examples, a method of treating a lesion in a body lumen may include (a) positioning a catheter adjacent to the lesion, the catheter having an emitter assembly including at least one shock wave generating region comprising a shock absorber made at least in part of a material having a Shore A hardness no greater than 100 and an enclosure surrounding the emitter assembly; (b) filling the enclosure with a fluid; and (c) generating a shock wave by applying a high energy pulse to the emitter assembly, wherein the shock wave exerts no less than 50 atm of pressure to the lesion. The shock absorber material may be a thermoplastic polyurethane. The shock absorber material may be an electrically insulating material. The step of filling the enclosure with fluid may include filling the enclosure with fluid to a pressure no more than 5 atm.

Any of the exemplary systems above can be used with any of the example catheters above. Additionally, any of the example catheters and systems above can be used for performing any of the methods above. Accordingly, any of the systems, catheters, and methods described above may be combined, in whole or in part, with one another and/or with any other features or characteristics described elsewhere herein.

BRIEF DESCRIPTION OF THE FIGURES

The invention will now be described, by way of example only, with reference to the accompanying drawings, in which:

FIG. 4A illustrates a perspective view, FIG. 4B illustrates a distal end view, and FIG. 4C illustrates a cross-sectional view.

FIG. 7 illustrates a method for treating a lesion with shock waves according to one or more aspects of the present disclosure.

FIG. 8 illustrates another method for treating a lesion with shock waves according to one or more aspects of the present disclosure.

DETAILED DESCRIPTION

Figure 1:
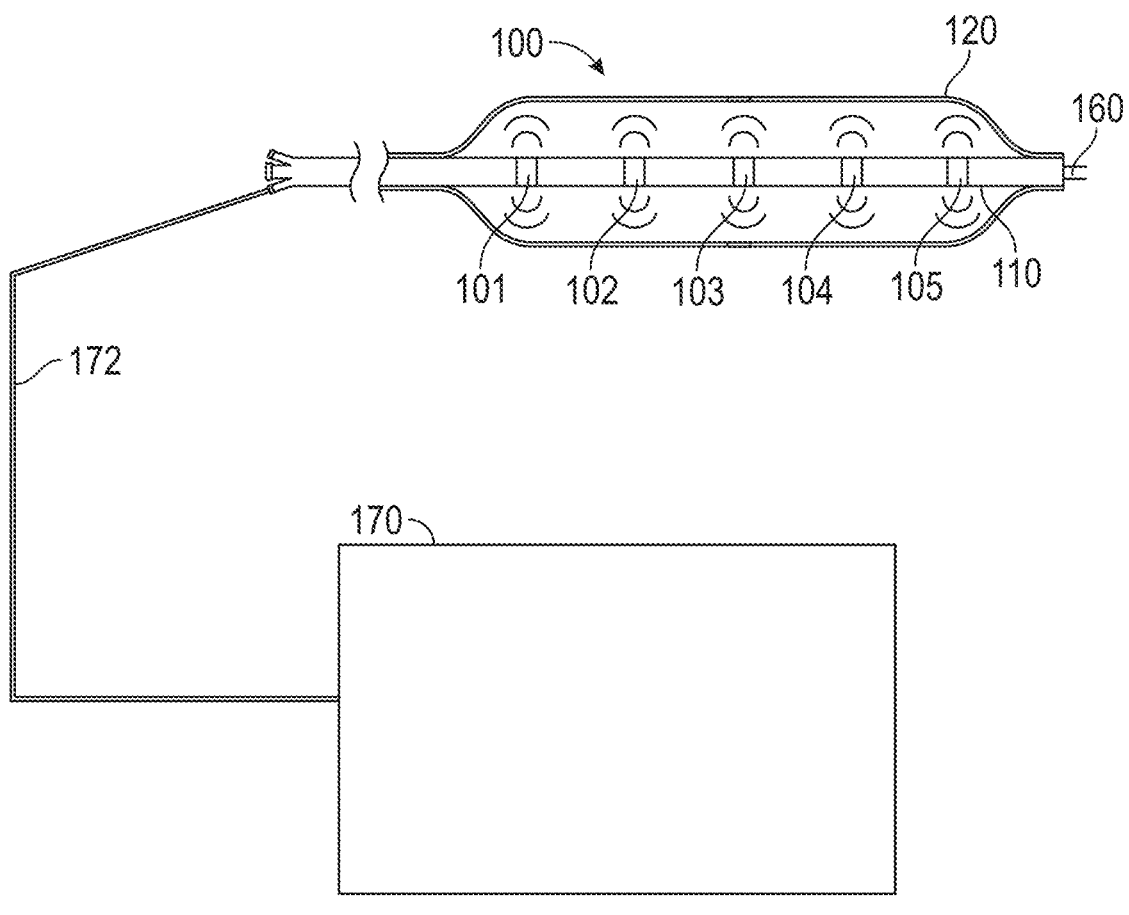
FIG. 1 illustrates an exemplary system comprising a catheter and a pulse generator according to one or more aspects of the present disclosure.

The following description is presented to enable a person of ordinary skill in the art to make and use the various embodiments and aspects thereof disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments and aspects thereof. Thus, the various embodiments and aspects thereof are not intended to be limited to the examples described herein and shown but are to be accorded the scope consistent with the claims.

As provided herein, it should be appreciated that any disclosure of a numerical range describing dimensions or measurements such as thicknesses, length, weight, time, frequency, temperature, voltage, current, angle, etc. is inclusive of any numerical increment or gradient within the ranges set forth relative to the given dimension or measurement. Furthermore, numerical designators such as "first," "second," "third," "fourth," etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

The present disclosure relates generally to a catheter system for treating stenosis of the aortic valve and lesions in other body lumens. The catheter system may include one or more shock wave generating regions that emit shock waves and/or cavitation bubbles for cracking lesions (e.g., calcified, fibrotic, or thrombic lesions). As described in more detail below, the catheter system may include a shock absorber that is made of a low durometer material. The addition of a shock absorber makes the catheter system more durable and capable of generating and withstanding shock waves with high sonic output. The shock absorber may also be used to increase the longevity of the shock wave generating region and, thus, the catheter itself. The catheter system may also include a relatively low durometer adhesive.

IVL catheter systems generate plasma, heat, and pressure every time the system applies therapy, i.e., when a cavitation bubble is formed and/or a shock wave is generated. At some operating parameters, the energies that are used to apply therapy may result in levels of generated plasma, heat, and pressure that can quickly degrade or displace the structures (e.g., electrohydraulic electrode assemblies) which are used to generate the shock wave for IVL. The shock absorber in part improves the durability and longevity of the catheter system by distributing or redirecting pressure that would otherwise impact, degrade, or displace the shock wave generating structures or other parts of the catheter. In this regard, the shock absorber operates as a structural pressure dampener or structural stabilizer to the shock wave generating structures (e.g., the emitter assemblies described in more detail below). In other words, incorporating a shock absorber in a shock wave generating structure dampens or reduces the amount of pressure that reaches and impacts the shock wave generating structures. However, the term "shock absorber" is not intended to imply that these structural features dampens or lessens sonic output from the device (i.e., the pressure exerted during treatment). Moreover, the selection of the material of the shock absorber may also be heat resistant, mitigating degradation from heat generated during the application of therapy.

FIG. 1 illustrates an exemplary IVL catheter system according to one or more aspects of the disclosure. The catheter system includes a catheter 100, an energy guide 172 for routing energy to the catheter 100, and a power source 170. The catheter 100 includes a central tube 110 having a guide wire lumen for guiding the catheter 100 along a guide wire 160 to the treatment site and an enclosure 120. The catheter 100 includes shock wave generating regions 101, 102, 103, 104, and 105 that are located along the central tube 100. In response to delivery of energy from the power source 170, one or more shock waves are generated from one or more of the shock wave generating regions 101, 102, 103, 104, and 105. The catheter 100 may be configured to selectively emit shock waves from one or more of the shock wave generating regions, in alternating sequence or at the same time. Although five shock wave generating regions are shown in FIG. 1, fewer shock wave generating regions (e.g., one, two, three, or four shock wave generating regions) may be included in shorter catheters for treating shorter lesions or more shock wave generating regions may be included in longer catheters for treating longer lesions.

Exemplary IVL catheter systems (such as the one shown in FIG. 1) are used for treating lesions in body lumens. In various examples, a lesion could be a calcified region of vasculature, a thrombus or an occlusion in vasculature, arteriosclerotic plaque, or a lesion in some other body lumen, such as a kidney stone in a ureter.

In one or more embodiments, each of the one or more of the shock wave generating regions 101, 102, 103, 104, and 105 includes an electrode assembly, which includes one or more electrode pairs. As used herein, the term "electrode" refers to an electrically conducting element (typically made of metal) that receives electrical current and subsequently releases the electrical current to another electrically conducting element. In the context of the present disclosure, electrodes are often positioned relative to each other, such as in an arrangement of an inner electrode and an outer electrode. Accordingly, as used herein, the term "electrode pair" refers to two electrodes that are positioned adjacent to and spaced apart each other such that application of a sufficiently high voltage to the electrode pair will cause an electrical current to transmit across the gap (also referred to as a "spark gap") between the two electrodes (e.g., from an inner electrode to an outer electrode, or vice versa, optionally with the electricity passing through a conductive fluid or gas therebetween). In some contexts, one or more electrode pairs may also be referred to as an electrode assembly. In the context of the present disclosure, the term "emitter" broadly refers to the area of an electrode assembly where the current transmits across the electrode pair, generating a shock wave. The terms "emitter sheath" and "emitter band" refers to a continuous or discontinuous band of conductive material that may form one or more electrodes of one or more electrode pairs, thereby forming a location of one or more emitters.

The shock wave generating regions 101, 102, 103, 104, and 105 additionally or alternatively may comprise a laser and optical fibers as a shock wave emitter system whereby the laser source delivers energy through an optical fiber and into a fluid to form shock waves and/or cavitation bubbles. Accordingly, although some shock wave devices described herein generate shock waves based on high voltage pulses applied to electrodes, it should be understood that a shock wave device may additionally or alternatively use laser pulses transmitted through optical fibers to generate shock waves and that the "emitters", "electrodes", and "electrode pairs" described herein may instead include output ends of optical fibers. These examples are not intended to be a comprehensive list of potential power sources to create shock waves in shock wave catheters.

In one or more embodiments of the present disclosure, the power source 170 shown in FIG. 1 includes a high voltage pulse generator. In one or more embodiments, the power source 170 supplies a high voltage pulse no less than six kilovolts (6 kV). In one or more embodiments, the power source 170 supplies a high voltage pulse no less than ten kilovolts (10 kV). In one or more embodiments, the power source 170 supplies a high voltage pulse between three kilovolts (3 kV) and twenty kilovolts (20 kV). In one or more embodiments, the power source 170 supplies a high voltage pulse between six kilovolts (6 kV) and ten kilovolts (10 kV). In one or more embodiments, the power source 170 is configured to supply a high voltage pulse that is adjustable in intensity. As explained above, the application of a relatively high voltage pulse (e.g., greater than 6 kV) may be beneficial for treating certain types of lesions (e.g., lesions associated with aortic valve stenosis) that necessitate a higher sonic output for treatment.

The enclosure 120 shown in FIG. 1, in one or more embodiments, is a balloon (e.g., an angioplasty balloon). The enclosure 120 may be in a collapsed or deflated configuration to provide a lower profile during delivery to the treatment site. During treatment, the enclosure 120 is inflated to a pressure between two and four atmospheres (2 atm-4 atm) with a liquid fluid (e.g., saline). Energy is then provided to shock wave generating regions 101, 102, 103, 104, and 105 resulting in the generation of one or more shock waves. The enclosure may then be deflated and reinflated to flush out any accumulated gas bubbles before further treatment at that site. The enclosure 120 may alternatively be advanced further to a different lesion (or different section of the same lesion) or withdrawn from the patient.

Figure 2:
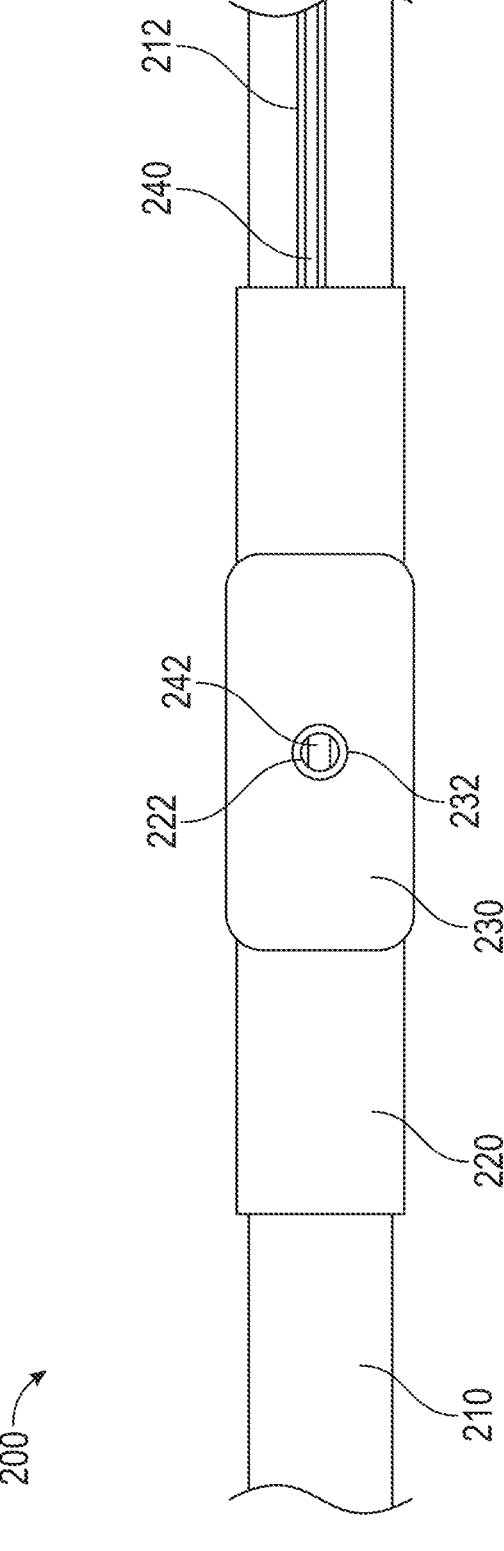
FIG. 2 illustrates an exemplary emitter assembly of a catheter according to one or more aspects of the present disclosure.
Figure 2:
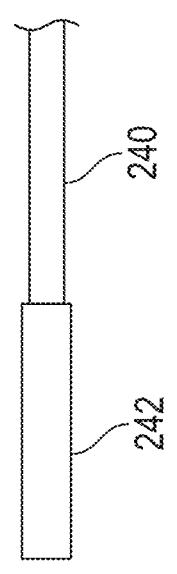

One or more of the shock wave generating regions 101, 102, 103, 104, and 105 may include an electrode assembly. FIG. 2 illustrates an exemplary electrode assembly 200 that includes a central tube 210, an inner electrode 242, a shock absorber 220, an outer electrode 230. The shock absorber 220, which is made of an electrically insulating material, includes an aperture 222. The outer electrode 230 includes an aperture 232 that is aligned with the aperture 222. The outer electrode 230 and the inner electrode 242 form an electrode pair that, when a high voltage is applied across the electrode pair (i.e., through the aligned apertures), generates a shock wave that propagates away from the central tube. A second inner electrode and aligned apertures may be located on a circumferentially opposite side of the electrode assembly 200.

In various embodiments of the present disclosure, a catheter for use in intravascular lithotripsy (IVL) includes a shock absorber such as the shock absorber 220. As noted above, the term "shock absorber" is used to describe a structural feature of an IVL catheter that can effectively reduce any destructive impact of acoustic pressure waves (e.g., shock waves) to a shock wave generating region of the catheter.

In various embodiments, a shock absorber is made of a material that has a Shore A hardness less than 100. In one or more embodiments, a shock absorber is made of a material that has a Shore A hardness less than 90. In one or more embodiments, a shock absorber is made of a material that has a Shore A hardness less than 75. In some embodiments, a shock absorber is made of a material that has a Shore A hardness no less than 20. Herein, material hardness is in accordance with ISO 48-4:2018. Such relatively softer materials have an acoustic impedance that is better suited to withstand the high pressures associated with shock waves when compared to relatively harder materials such as polyimide.

In some embodiments, a shock absorber (e.g., a shock absorbing layer) for a shock wave catheter is made of a material that has a flexural modulus less than 1 GPa. In some embodiments, the flexural modulus is no greater than 0.25 GPa. In other embodiments, the flexural modulus is no greater than 50 MPa. Herein, flexural modulus of a material is determined in accordance with ISO 178:2019.

In one or more embodiments, a shock absorber is made of an elastomeric material. An elastomeric material can include various thermoplastic polyurethanes (TPUs), rubbers, silicones, fluoropolymers (e.g., polytetrafluoroethylene), or other materials having similar elastomeric properties. In particular, TPUs may be effective for their versatility in manufacturing and relatively low cost when compared to materials such as polyimide. Further, including such elastomeric materials in an IVL catheter may improve its flexibility and thus navigability through body lumens.

As noted above, incorporating a shock absorber into a shock wave generating structure can greatly improve longevity (i.e., the number of shock wave pulses the structure can generate before failure due to deterioration) of the structure (and, thus, the device). For example, incorporating the shock absorber in place of higher durometer insulating material can increase the longevity of the shock wave generating structure ten-fold.

Figure 3A:
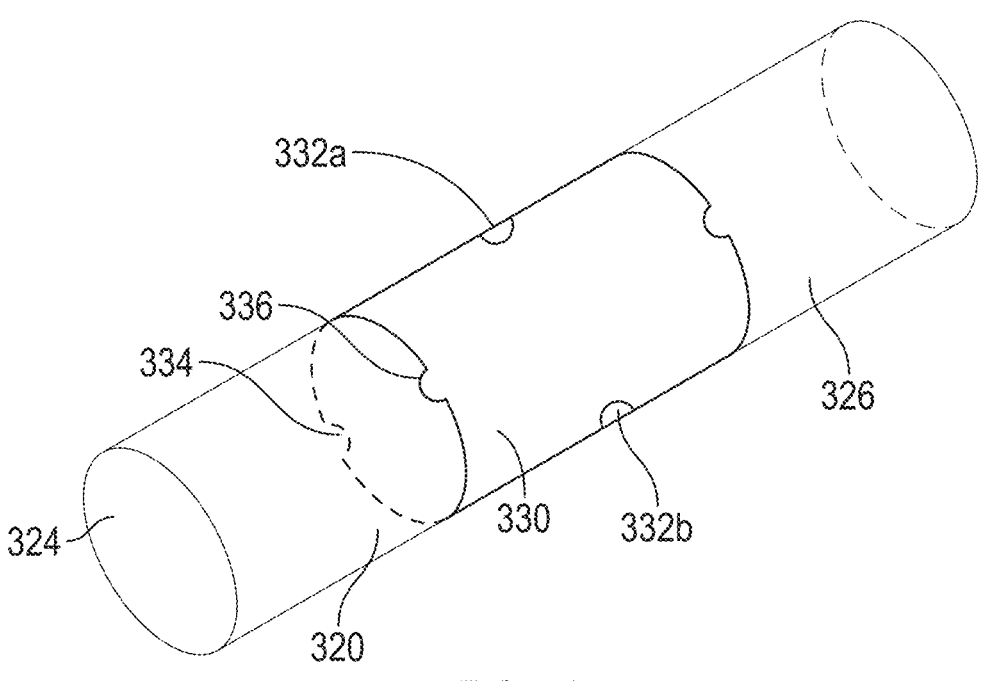
FIGS. 3A and 3B illustrate an exemplary conductive sheath and a shock absorber of an exemplary emitter assembly according to one or more aspects of the present disclosure.
Figure 3B:
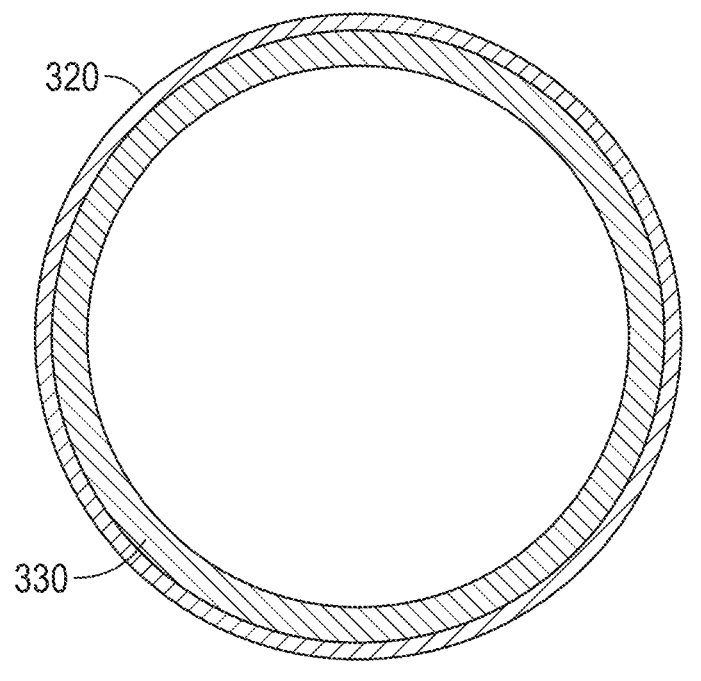

FIGS. 3A and 3B illustrate an exemplary shock absorber 320 overlaid with an outer band 330, according to one or more aspects of the present disclosure. FIG. 3A is a perspective view and FIG. 3B is a cross sectional view through the shock absorber 320 and outer band 320. The shock absorber 320 and outer band 330 may be part of an electrode assembly (such as electrode assembly 200), where the outer band 330 is an electrode of an electrode pair that is configured to generate shock waves. In this embodiment, the outer band 330 is, at least in part, formed of an electrically conductive material (e.g., stainless steel, nickel, molybdenum, platinum, palladium, tungsten, iridium, copper, or alloys thereof).

In other embodiments, the shock absorber 320 is provided as a structural feature of a light energy (e.g., lasers) generated shock wave generating region. In such applications, the shock absorber 320 similarly improves durability of the shock wave generating region.

As shown in FIG. 3B, the shock absorber 320, in one or more embodiments, is thicker than the outer band 330. In one or more embodiments, the shock absorber 320 is 0.25 mm to 1.0 mm in thickness. In one or more embodiments, the shock absorber 320 is 0.3 mm to 0.6 mm in thickness. In other embodiments, the shock absorber 320 is no less than 0.5 mm in thickness.

In one or more embodiments, the shock absorber 320 is slightly compressed by outer band 330. The shock absorber 320 includes a shock absorbing layer that is at least partially surrounded by outer band 330. The outer diameter of the shock absorber 320 is 2.0 mm to 4.0 mm and the outer diameter of the outer band 330 is less than the outer diameter of the shock absorber, in one or more embodiments of the disclosure. In other embodiments, the shock absorber outer diameter is 3.0 mm to 4.0 mm, and the outer diameter of the outer band 330 is no greater than 3.0 mm. When the outer band 330 compresses the shock absorber 320, the outer band 330 can be better secured to the shock absorber 320, further improving the structural integrity of the assembly.

In one or more embodiments, shock absorber 320 has a distal portion 324 and a proximal portion 326. The overall length (from the proximal end to the distal end) of the shock absorber 320 is 2.0 mm to 10 mm and the proximal portion 324 and the distal portion 326 are each about 0.5 mm to about 3.0 mm in length. The outer band 330 has a length of 0.5 mm to 3.0 mm. In one or more embodiments, the overall length of shock absorber 320 is no less than 3.0 mm and the outer band has a length no more than 2.0 mm.

The outer band 330 includes apertures 332*a* and 332*b*, notches 334 and tabs 336. These features can help to secure outer band 330 more tightly to the shock absorber 330 when the outer band 320 slightly compresses the shock absorber 330. In embodiments where the outer band 330 is an electrode, these features may also provide edge surfaces where a spark gap is formed. In such embodiments, the shock absorber 320 includes aligned cutouts as openings between an inner electrode (not shown) and the outer band 330.

It should be understood that while shock absorber 320 is depicted in FIGS. 3A and 3B as being cylindrical in shape, other geometries are possible, including discontinuous sheaths and patches. Shock absorber 320 can additionally be formed with various apertures and cutouts (e.g., to provide gaps for current to pass from inner and outer electrodes). Similarly, the outer band 330 need not be a continuous band. For the sake of clarity in these figures, no interior lumen (e.g., a guide wire lumen, fluid lumen, or other lumens) or interior electrode surface are shown. However, it should be appreciated that the shock absorber is positioned at least in part between the outer lumen and either or both of an interior lumen and inner electrode surface.

Figure 4A:
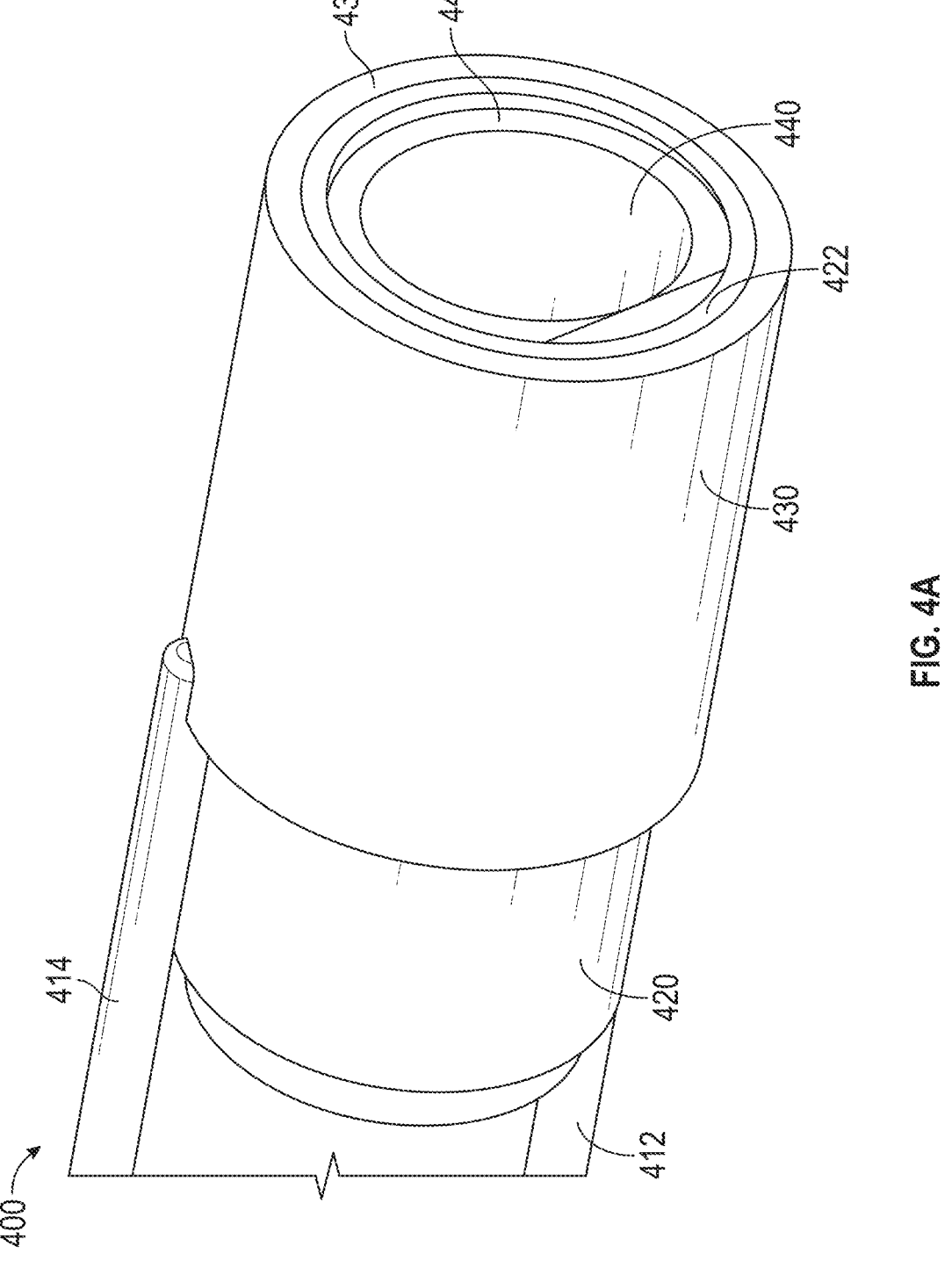
FIGS. 4A-4C illustrate another exemplary emitter assembly according to one or more aspects of the present disclosure.
Figure 4B:
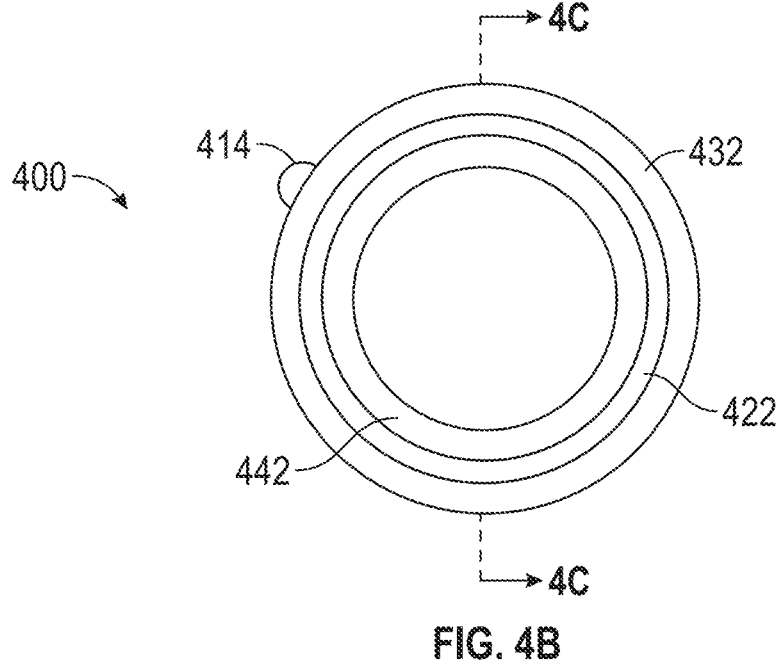
Figure 4C:
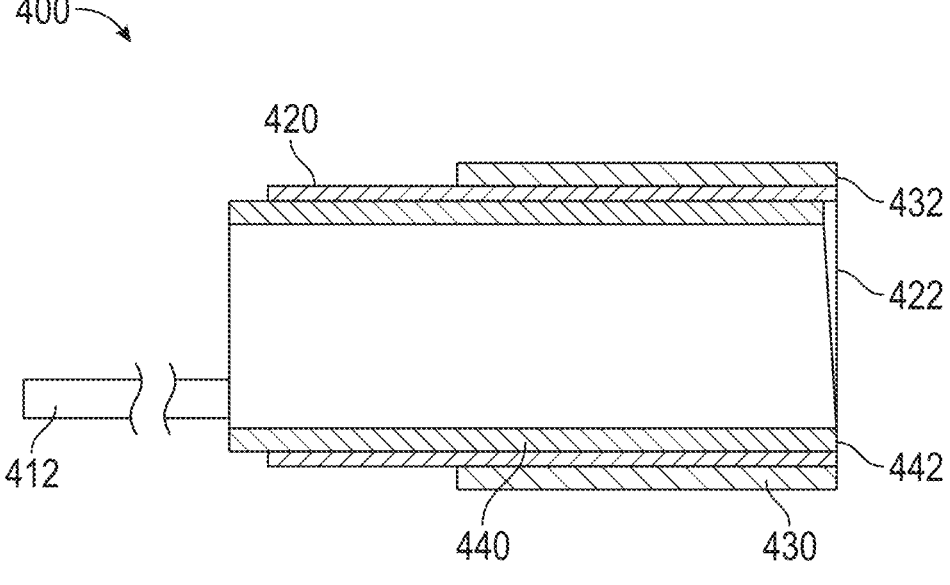

FIGS. 4A-4C illustrate a distal end of an exemplary electrode assembly 400 of a catheter designed to generate and direct shock waves and/or cavitation bubbles in a distal direction of the catheter according to one or more embodiments of the present disclosure. FIG. 4A is a perspective view, FIG. 4B is a distal end view, and FIG. 4C is a side cross-sectional view through plane 4C in FIG. 4B. The assembly 400 includes an inner conductive sheath 440 and an outer conductive sheath 430. The inner and outer conductive sheaths 440 and 430 are separated by a shock absorber 420 to provide an electrically insulating layer that can effectively withstand the high pressures associated with generating shock waves and cavitation bubbles. The inner conductive sheath 440 and the outer conductive sheath 430 respectively form inner and outer electrodes of an electrode pair. Wires 412 and 414, which extend from a high voltage power source (such as the power supply 170 in FIG. 1) along the length of the catheter, are electrically connected to the outer conductive sheath 430 and the inner conductive sheath 440, respectively. One of the wires 412 and 414 is connected to a negative terminal of the high voltage source and the other wire is connected to a positive terminal of the high voltage source. When a high voltage pulse is applied to the wires 412 and 414, current flows across a spark gap between the outer conductive sheath distal edge 432 and the inner conductive sheath distal edge 442, resulting in a shock wave and/or cavitation bubble. The outer conductive sheath distal edge 432 may be positioned at the same distal location as a shock absorber distal edge 422.

The dielectric properties and thickness of the shock absorber 420 allow for the shock absorber 420 to erode in a controlled manner as successive high voltage pulses erode parts of the conductive sheath edges. Further, the acoustic impedance of the shock absorber 420 is selected to better facilitate the transmission of acoustic pressure waves and improve the durability of the electrode assembly 400.

Figure 5:
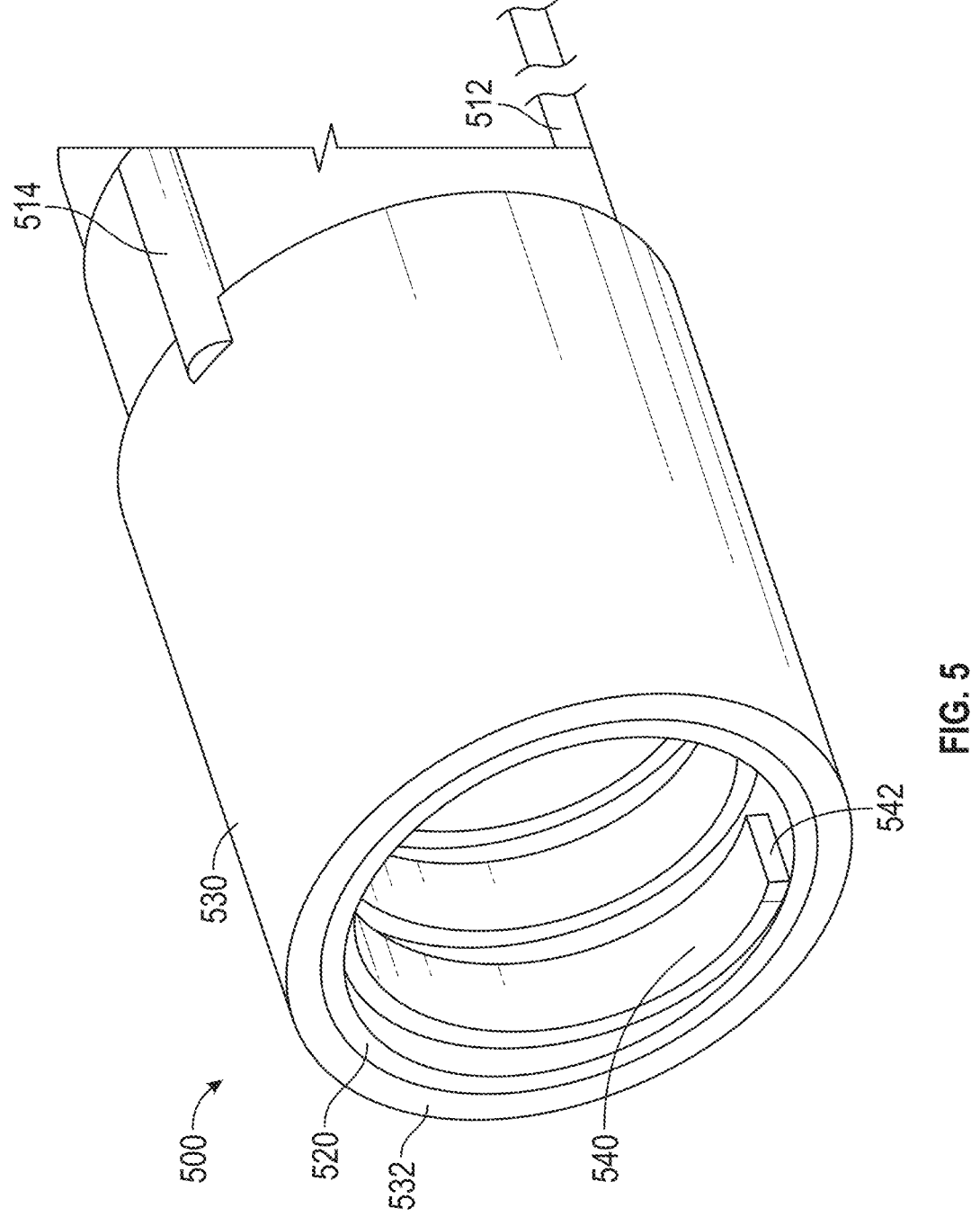
FIG. 5 illustrates another exemplary emitter assembly according to one or more aspects of the present disclosure.

FIG. 5 illustrates a distal end of another exemplary electrode assembly 500 of another catheter designed generate and direct shock waves or cavitation bubbles in a distal direction of the catheter according to one or more embodiments of the present disclosure. The assembly 500 includes an inner conductive coil 540 and an outer conductive sheath 530. The inner conductive coil 540 and the outer conductive sheath 530 are separated by a shock absorber 520 to provide an electrically insulating layer that can effectively withstand the high pressures associated with generating shock waves and cavitation bubbles. The inner conductive coil 540 and the outer conductive sheath 530 respectively form inner and outer electrodes of an electrode pair. Two wires extend from a high voltage power source (such as power supply 170 in FIG. 1) along the length of the catheter, are electrically connected to the outer conductive sheath 530 and the inner conductive coil 540. One of the wires is connected to a negative terminal of the high voltage source and the other wire is connected to a positive terminal of the high voltage source. When a high voltage pulse is applied to the wires 512 and 514, current flows across a spark gap between the outer conductive sheath distal edge 532 and the inner conductive coil distal end 542, resulting in a shock wave and/or cavitation bubble.

In alternative implementations, shock absorber material can be placed between the turns of a conductive coil, in the gap or pitch of the coil. In such embodiments, the lumen between the conductive coil and the conductive sheath can be an electrically insulating layer or a further layer of shock absorber material.

Similar to the embodiments described above, the shock absorber 520 functions to both insulate conductive components of the electrode assembly from each other and, importantly, to provide a medium through which acoustic waves may be effectively transmitted. In the embodiment shown in FIG. 5, the shock absorber 520 may also have a suitable breakdown voltage such that the shock absorber 520 erodes upon application of a high voltage pulse across the electrode pair. As the electrode material also erodes at the site of the spark gap upon application of a high voltage pulse, an optimal spacing between the electrodes of the electrode pair (i.e., the distance between the outer conductive sheath edge 532 and the inner conductive coil distal end 542) may be maintained upon successive applications of a high voltage pulse.

In one or more embodiments, a shock wave catheter includes a low durometer adhesive. A low durometer adhesive may include an adhesive that (upon curing) has a Shore A hardness less than 100. In some examples, the low durometer adhesive has a Shore A hardness less than 50. The low durometer adhesive may be applied to adhere components of shock wave generating regions together. In one or more embodiments, a low durometer adhesive includes a cyanoacrylate (e.g., an ethyl and octyl cyanoacrylate). In one or more embodiments, a low durometer adhesive includes a silicone. For example, the low durometer adhesive may be applied to fix the positions of conductive bands or sheaths (such as those described above) to insulating layers or shock absorbers.

Figure 6:
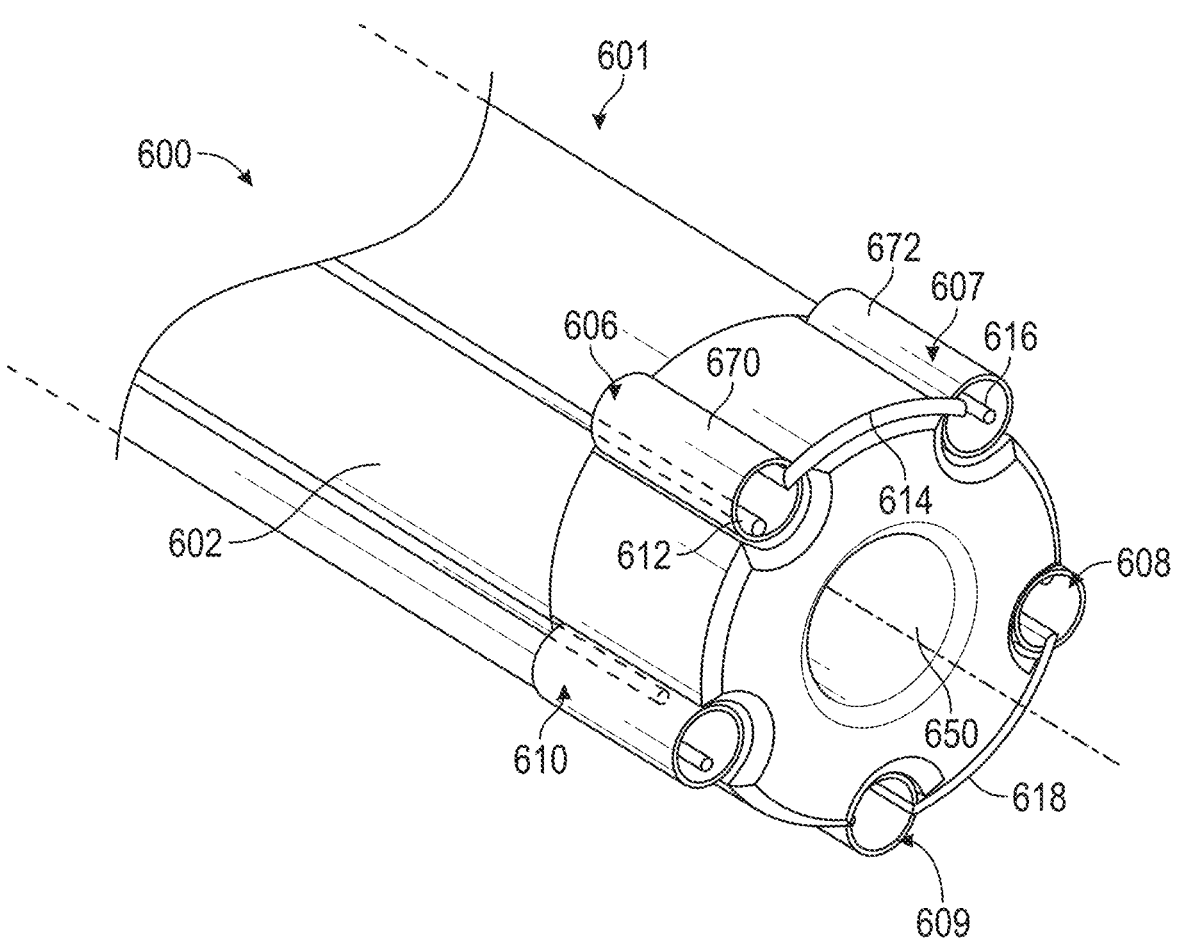
FIG. 6 illustrates an exemplary catheter according to one or more aspects of the present disclosure.

FIG. 6 illustrates a distal region of catheter 600 designed to generate and direct shock waves or cavitation bubbles in a distal direction of the catheter 600 according to one or more embodiments of the present disclosure. In some embodiments, catheter 600 includes a catheter body 601 that includes, at least in a distal region, a shock absorber 602. The shock absorber 602 may be included as an outer layer of the catheter body 601 or may be integrally formed as part of the catheter body 601 as shown in FIG. 6. Catheter 600 includes shock wave emitters 606-610. Each of the shock wave emitters 606-610 can include a first electrode (e.g., conductive sheaths 670, 672) and a second electrode (e.g., insulated wires having conductive distal ends 612). The first and second electrodes form an electrode pair spaced apart by a spark gap. When voltage is applied across the electrode pair (e.g., by current delivered or carried away by wires 612 and 616 to a power supply), a shock wave is generated. Shock wave emitters 606-610 may be connected to one or more of each other in series (e.g., by wires 614, 618) such that current is delivered from a power source to a first electrode pair (e.g., conductive sheath 670 and exposed end of wire 612), then to a second electrode pair (e.g., conductive sheath 672 and exposed end of insulated wire 616), and either back to the power source or a third electrode pair. Catheter 600 additionally includes a guidewire lumen 650, which can be used to deliver catheter 600 to a treatment site.

Advantageously, the catheter 600 can be configured such that shock waves emitted from the shock wave emitters 606-610 constructively interfere and amplify the sonic output generated by the device. As such, the pressures generated by such a catheter having a plurality of distally directed shock wave emitters may be substantially higher than if only a single shock wave emitter was included. Shock absorber 602 may thus be important to increasing the durability and longevity of catheter 600, particularly at the region of the shock wave emitters 606-610.

While catheter 600 is shown with each shock wave emitter formed by a conductive sheath and an exposed end of an insulated wire, in other embodiments, each electrode pair of a shock wave emitter is formed by exposed ends of conductive wires. In some embodiments, catheter 600 includes a distal enclosure that defines a chamber housing one or more of the shock wave emitters 606-610. In other embodiments, there is no enclosure, and the shock wave emitters emit shock waves directly within the body lumen. In such embodiments, catheter body 601 may be provided with an additional aspiration lumen to remove debris generated by the shock wave treatment.

FIG. 7 illustrates a method of treating a lesion with a catheter having a shock absorber according to one or more aspects of the disclosure. The method includes, at step 701, navigating an IVL catheter and positioning it adjacent to a lesion (e.g., a calcified artery or heart valve). The IVL catheter includes a shock wave emitter assembly and a shock absorber similar to the embodiments described above. At step 702, one or more high voltage pulses no less than a minimum voltage are applied to the emitter assembly. The minimum voltage is no less than 6 kV. In some embodiments, the minimum voltage is no less than 10 kV. Application of the high voltage pulse results in the generation of one or more shock wave from the emitter assembly. Optionally, steps 701 and 702 can be repeated to treat a different region of the lesion or to treat a different lesion.

FIG. 8 illustrates another method of treating a lesion with a catheter having a shock absorber according to one or more aspects of the disclosure. At step 801, an IVL catheter is positioned adjacent to a lesion (e.g., a calcified artery or heart valve). The IVL catheter includes a shock absorber, an enclosure, and an emitter assembly. The shock absorber is made of a low durometer material as described above. The emitter assembly can include one or more electrode pairs for generating shock waves. In some embodiments, the emitter assembly includes one or more ends of optical fibers that deliver light energy for generating shock waves electromagnetically. At step 802, the enclosure is filled with a fluid. The fluid may be a conductive fluid such as saline. The fluid may include an x-ray imaging contrast agent such as iodinated contrast agents. In some embodiments, the enclosure is a balloon that is inflated to a pressure less than 5 atm. At step 803, one or more high energy pulses (e.g., a high voltage pulse no less than 10 kV) are applied to the emitter assembly. The emitter assembly generates one or more shock waves that exert no less than 50 atm of pressure to the lesion. Following shock wave treatment, the enclosure is deflated. In some examples, the enclosure may be refilled with fluid and the lesion may be treated with additional shock waves. Optionally, steps 801-803 are repeated at a different region of the lesion or to treat a different lesion.

In other embodiments, distally firing catheters include distally directed ends of light guides (e.g., optical fibers) and a shock absorber such as those described above. In such embodiments, the shock absorber helps stabilize the structure of the distal end of a catheter without dampening the acoustic output.

Although the electrode assemblies and catheter devices described herein have been discussed primarily in the context of treating coronary occlusions, such as lesions in vasculature, the electrode assemblies and catheters herein can be used for a variety of occlusions, such as occlusions in the peripheral vasculature (e.g., above-the-knee, below-the-knee, iliac, carotid, etc.). For further examples, similar designs may be used for treating soft tissues, such as cancer and tumors (i.e., non-thermal ablation methods), blood clots, fibroids, cysts, organs, scar and fibrotic tissue removal, or other tissue destruction and removal. Electrode assembly and catheter designs could also be used for neurostimulation treatments, targeted drug delivery, treatments of tumors in body lumens (e.g., tumors in blood vessels, the esophagus, intestines, stomach, or vagina), wound treatment, non-surgical removal and destruction of tissue, or used in place of thermal treatments or cauterization for venous insufficiency and fallopian ligation (i.e., for permanent female contraception).

In one or more examples, the electrode assemblies and catheters described herein could also be used for tissue engineering methods, for instance, for mechanical tissue decellularization to create a bioactive scaffold in which new cells (e.g., exogenous or endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

In some embodiments, an IVL catheter is a so-called "rapid exchange-type" ("Rx") catheter provided with an opening portion through which a guide wire is guided (e.g., through a middle portion of a central tube in a longitudinal direction). In other embodiments, an IVL catheter may be an "over-the-wire-type" ("OTW") catheter in which a guide wire lumen is formed throughout the overall length of the catheter, and a guide wire is guided through the proximal end of a hub.

It should be noted that the elements and features of the example catheters illustrated throughout this specification and drawings may be rearranged, recombined, and modified without departing from the present invention. For instance, while this specification and drawings describe and illustrate catheters having several example emitter assembly designs, the present disclosure is intended to include catheters having a variety of emitter assembly configurations. The number, placement, and spacing of the electrode pairs of the shock wave generators can be modified without departing from the subject invention. Further, the number, placement, and spacing of enclosures of catheters can be modified without departing from the subject invention.

It should be understood that the foregoing is only illustrative, and that various modifications, alterations and combinations can be made by those skilled in the art without departing from the scope and spirit of the disclosure. Any of the variations of the various catheters disclosed herein can include features described by any other catheters or combination of catheters herein. Furthermore, any of the methods can be used with any of the catheters disclosed. Accordingly, it is not intended that the systems, catheters, and methods described herein be limited, except as by the appended claims.

The invention claimed is:

1. A catheter for treating lesions in a body lumen, the catheter comprising:
    an elongate member;
    at least one shock wave emitter assembly mounted over a distal portion of the elongate member, the at least one shock wave emitter assembly comprising
        an electrode pair comprising:
            an inner electrode; and
            an outer electrode, the at least one shock wave emitter assembly configured to generate a shock wave when a voltage of no less than 10 kV is applied across the electrode pair; and
        a shock absorber located at least partially between the inner electrode and the outer electrode and surrounding the inner electrode and having an aperture aligned with the inner electrode;
        wherein the shock absorber comprises a polymer material having a Shore A hardness value between 20 and 75, and the shock absorber is between 0.25 millimeters and 1.0 millimeters thick.

2. The catheter of claim 1, wherein the polymer material is a thermoplastic polyurethane.

3. The catheter of claim 1, wherein the polymer material has a Shore A hardness value no less than 50.

4. The catheter of claim 1, further comprising an enclosure that at least partially surrounds the at least one shock wave emitter assembly, wherein shock waves are transmitted through a wall of the enclosure.

5. The catheter of claim 4, wherein the enclosure comprises a balloon.

6. The catheter of claim 1, wherein the polymer material is an electrically insulating material.

7. The catheter of claim 1, wherein the at least one shock wave emitter assembly is electrically connected to a power supply configured to generate a generator voltage no less than 6 kV.

8. A catheter system for treating lesions in a body lumen, the system comprising:
    a catheter comprising:
        an elongate member;
        at least one shock wave emitter assembly mounted over a distal portion of the elongate member, the at least one shock wave emitter assembly comprising:
        an inner electrode;
        a shock absorber at least partially surrounding the inner electrode and having a shock absorber aperture aligned with the inner electrode, wherein the shock absorber comprises a polymer material having a Shore A hardness value between 20 and 75, the shock absorber is between 0.25 millimeters and 1.0 millimeters thick; and
        a conductive band comprising an outer electrode that is aligned with the shock absorber aperture, the inner electrode and the outer electrode forming an electrode pair; and
    a power supply electrically connected to the at least one shock wave emitter assembly and configured to supply a voltage no less than 10 kV to the at least one shock wave emitter assembly.

9. The catheter system of claim 8, wherein the shock absorber comprises a thermoplastic polyurethane.

10. The catheter system of claim 8, wherein the polymer material has a Shore A hardness value no less than 50.

11. The catheter system of claim 8, wherein the polymer material is an electrically insulating polymer material.

12. The catheter system of claim 8, further comprising an enclosure that at least partially surrounds the at least one shock wave emitter assembly, wherein shock waves are transmitted through a wall of the enclosure.

13. The catheter system of claim 12, wherein the enclosure comprises a balloon.

14. A catheter for treating lesions in a body lumen, the catheter comprising:
    an elongate member;
    at least one shock wave emitter assembly located at a distal portion of the elongate member, the at least one shock wave emitter assembly comprising:
        an electrode pair comprising:
            a first electrode electrically connected to a high voltage power source configured to supply a voltage no less than 10 kV to the electrode pair; and
            a second electrode spaced apart from the first electrode and electrically connected to the high voltage power source, the at least one shock wave emitter assembly configured to generate a shock wave when a voltage is applied across the electrode pair; and
        a shock absorber at least partially located between the first electrode and the second electrode,
    wherein:
        the shock absorber comprises a polymer material having a Shore A hardness value between 20 and 75 and is between 0.25 millimeters and 1.0 millimeters thick, and
        the first electrode comprises an edge of a conductive sheath, wherein an overall length of the shock absorber is no less than 3.0 millimeters and an overall length of the conductive sheath is no more than 2.0 millimeters.

15. A catheter for treating lesions in a body lumen, the catheter comprising:
    an elongate member;
    a plurality of axially aligned shock wave emitter assemblies located at a distal portion of the elongate member, each of the plurality of shock wave emitter assemblies comprising:
        an electrode pair comprising:
            a first electrode electrically connected to a high voltage power source configured to supply a voltage no less than 10 kV to the electrode pair; and
            a second electrode spaced apart from the first electrode and electrically connected to the high voltage power source, the plurality of shock wave emitter assemblies configured to generate a shock wave when a voltage is applied across the electrode pair; and
        a shock absorber at least partially located between the first electrode and the second electrode,
    wherein:
        the shock absorber comprises a polymer material having a Shore A hardness value between 20 and 75 and the shock absorber is between 0.25 millimeters and 1.0 millimeters thick.

\* \* \* \* \*